United States Patent

Klodowski et al.

[11] Patent Number: 5,122,341
[45] Date of Patent: Jun. 16, 1992

[54] DEVICE FOR GAS CONTAMINANT TESTER TRAINING

[75] Inventors: Harry F. Klodowski, E. Syracuse; Philip A. Hider, Marcellus; Patricia A. Morin, E. Syracuse, all of N.Y.

[73] Assignee: Carrier Corporation, Syracuse, N.Y.

[21] Appl. No.: 599,165

[22] Filed: Oct. 17, 1990

[51] Int. Cl.⁵ .................... G01N 31/00; G01N 1/00
[52] U.S. Cl. .................... 422/61; 422/104; 422/102; 422/86; 422/88; 73/23.2; 73/432.1; 434/298; 434/429; 434/219
[58] Field of Search .............. 422/61, 86, 88, 102, 422/103, 104; 73/1 J, 866.4, 434, 23.2, 432.1; 434/298, 429, 219

[56] References Cited

U.S. PATENT DOCUMENTS

| | | | |
|---|---|---|---|
| 3,497,320 | 2/1970 | Blackburn et al. | 422/61 |
| 3,676,072 | 7/1972 | Krivis | 422/61 |
| 3,676,073 | 7/1972 | Luckey | 422/61 |
| 3,903,745 | 9/1975 | Bolser | 73/864.91 |
| 4,173,886 | 11/1979 | Archbold et al. | 73/864.73 |
| 4,786,472 | 11/1988 | McConnell et al. | 422/61 |

Primary Examiner—James C. Housel
Assistant Examiner—Long V. Le

[57] ABSTRACT

A device for demonstrating the operation of gas contaminant testing apparatus and for training persons to use such apparatus. The device can be portable and allows demonstration of and training on testing apparatus in a location removed from the environment in which the gaseous medium and its gaseous and vaporous contaminants are normally found. The device uses very small contaminant samples for demonstration in order to minimize personnel exposure and inadvertent or deliberate releases to the environment. The device allows the substitutions of, for training and demonstration purposes, a harmless gaseous medium for the actual gaseous medium of interest. In a preferred embodiment, designed for demonstrating the operation of a refrigerant contaminant testing apparatus, air is susbstituted for refrigerant as the gaseous medium in which contaminants are entrained when using the device. In that embodiment, air is caused to flow through a container holding a contaminant sample of interest. Vapors of the contaminant mix with the air and the mixture is caused to flow through a refrigerant contaminant testing tube connected to the device, resulting in testing tube indications that emulate the indications to be expected when testing a refrigerant sample containing the contaminant. More than one sample container can be fitted into the device and there can be one or more tester connections. The sample containers are interchangeable so that demonstrating a variety of contaminants is possible. The device may be used as an adjunct to gas testing apparatus for testing a gas sample collected at a remote location.

7 Claims, 2 Drawing Sheets

DEVICE FOR GAS CONTAMINANT TESTER TRAINING

BACKGROUND OF THE INVENTION

This invention relates to the field of gas testing apparatus. More particularly, the invention relates to a device for demonstrating gas contaminant testing apparatus for training or other purposes.

Gas contaminant testing apparatus of different kinds are used in a variety of applications and for testing for a large number of different contaminants. One relatively common type is used for detecting contaminants such as carbon dioxide, carbon monoxide and hydrogen in atmospheric air. Another type is used for the detection of gaseous and vaporous contaminants, such as water and acids, in refrigerants. Still other types are available to detect other gaseous and vaporous contaminants in air or other gases. Many kinds of apparatus can not only detect the presence but also measure the concentration of contaminants.

Frequently, the contaminants for which a specific testing apparatus is designed to detect are toxic or hazardous. Further, the gaseous medium in which the contaminant gases are entrained may itself be toxic or hazardous. Many refrigerants now in widespread use, for example, have been evaluated to be environmental hazards. Yet persons who handle and work with gases and gas testing apparatus require training to ensure proper operation and efficient use of the apparatus as well as accurate and meaningful test results. At present, the commonplace method to demonstrate a gas testing apparatus is to place the sensor portion of the apparatus in or near the mouth of an open container containing a volatile liquid or the discharge from a pressurized gas cylinder. In employing methods such as these, persons conducting and observing the demonstration are exposed to possibly hazardous fumes or gases and those fumes or gases escape to the atmosphere.

There is a need therefore for a means for providing realistic and effective training in contaminant testing apparatus operation while at the same time minimizing handling and personnel exposure to potentially toxic substances and the release of hazardous materials into the environment.

SUMMARY OF THE INVENTION

An object of the present invention is to enable training and demonstration in the operation and use of apparatus for testing for gaseous or vaporous contaminants entrained in a gaseous medium in a classroom or other location removed from the environment in which the predominant gas or the contaminants are normally found.

Another object of the present invention is to enable training on testing apparatus using the minimum amount of gases and volatile liquids necessary in order to reduce personnel exposure to potentially hazardous gases and vapors and to reduce the amount of such gases and vapors released to the environment either deliberately or inadvertently.

A further object of the present invention is to provide a testing apparatus training device that is economical to manufacture, rugged, portable and simple to operate.

The present invention attains these and other objects in a gas contaminant testing apparatus demonstration and training device. The device can be portable and allows demonstration of and training on testing apparatus in a classroom or other location removed from the environment in which the gaseous medium and its gaseous and vaporous contaminants are normally found. Since many contaminants are toxic or hazardous, the device uses very small contaminant samples for demonstration in order to minimize personnel exposure and inadvertent or deliberate releases to the environment. And, since gaseous media in which contaminants of interest are entrained may also be toxic or hazardous, the device allows the substitution of, for training and demonstration purposes, a harmless gaseous medium for the actual gaseous medium of interest.

In a preferred embodiment, designed for demonstrating the operation of a refrigerant contaminant testing apparatus, air is substituted for refrigerant as the gaseous medium in which contaminants are entrained when using the device. In that embodiment, air is caused to flow through a container holding a volatile liquid contaminant sample of interest. Vapors of the contaminant mix with the air, and the mixture is caused to flow through a refrigerant contaminant tester connected to the device, resulting in tester indications that emulate the indications to be expected when testing a refrigerant sample containing the contaminant. More than one sample container can be fitted into the device and there can be one or more tester connections. The sample containers are interchangeable so that demonstrating a variety of contaminants is possible. Sample containers may contain more than one contaminant so that diagnostic training is possible.

BRIEF DESCRIPTION OF THE DRAWINGS

The accompanying drawings form a part of the specification. Throughout the drawings, like reference numbers identify like elements.

DESCRIPTION OF THE PREFERRED EMBODIMENTS

Figure 1:
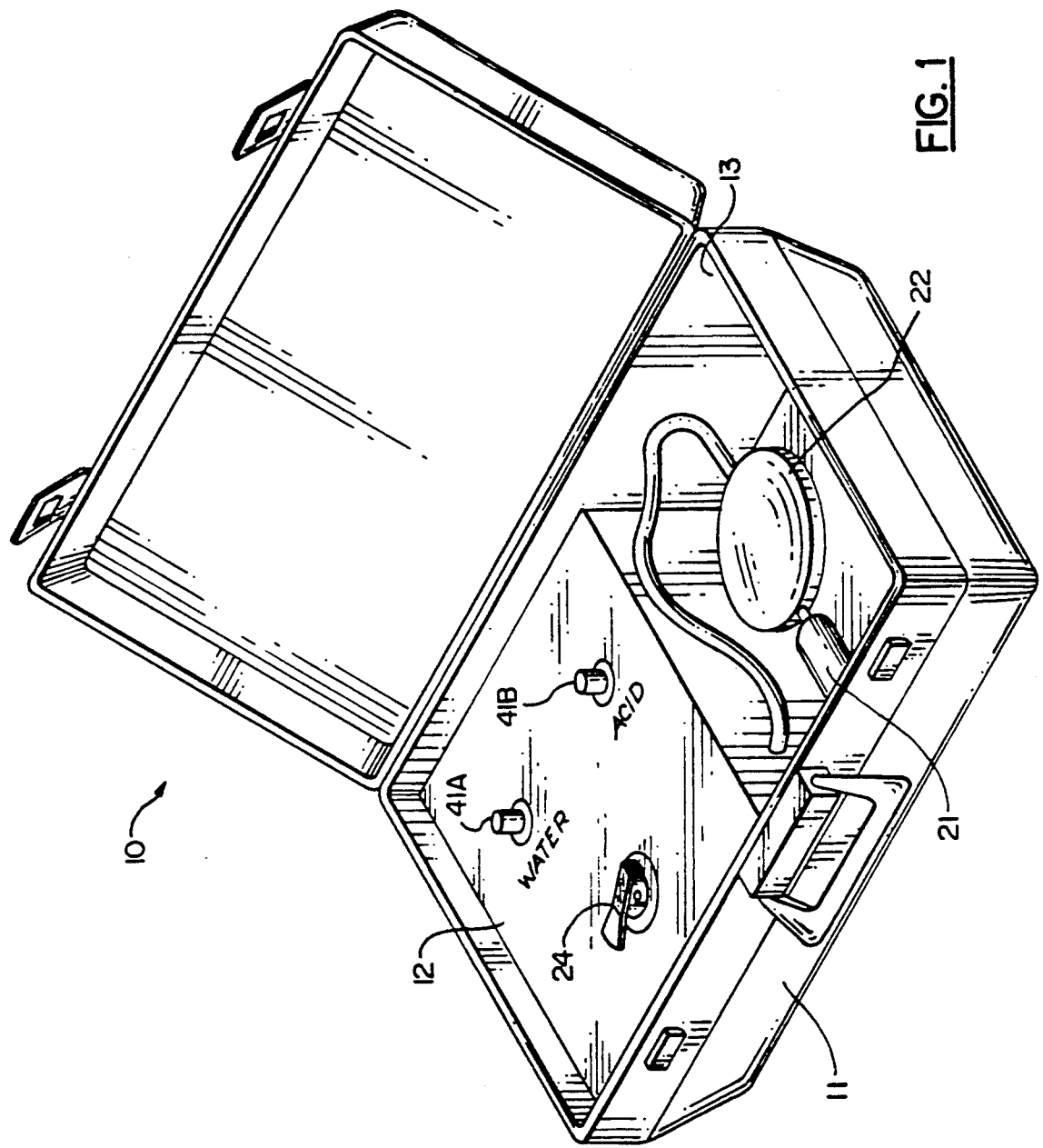
FIG. 1 is an overall pictorial view of a training device constructed in accordance with one embodiment of the invention.

Shown in FIG. 1 is a training device 10 designed and constructed according to the principles of the present invention. Training device 10 is specifically configured for use in demonstrating the use of an apparatus for detecting the presence of two contaminants, water and inorganic acid, that may be present in the refrigerant charge of an air conditioning, refrigeration or similar system. Such an apparatus is the Carrier TOTAL-TEST ® refrigerant tester.

The contaminant detection means in the TOTAL-TEST ® refrigerant tester is a testing tube that contains reagent chemicals, among them being one that changes color when in contact with water vapor and another one that changes color when in contact with acid vapors. In use, the testing tube is placed in a tube holder, which also contains a pressure reducing orifice, and connected to a closed, pressurized system containing a refrigerant. Refrigerant from the system is admitted into the tube holder where it first passes through the orifice and is depressurized to near atmospheric pressure and then passes through the testing tube. If any water or acid is entrained in the refrigerant, the presence and identification of the contaminant is indicated by a color change in the appropriate reagent chemical. Training device 10 simulates an air conditioning, refrigeration or similar system on which the TOTALTEST ® refrigerant tester might be used and allows the tester to be demonstrated or persons to be trained on its use at a location remote from an actual system containing refrigerant. In addition, air is substituted for refrigerant as the gas medium in which the containments are entrained so that there is no release of refrigerant to the environment due to use of the tester with the device.

All the components of training device 10 are contained in portable carrying case 11. Inside carrying case 11 are panel 12 and storage compartment 13. The only operating components of training device 10 that are visible when carrying case 11 is open and ready for use are tester connections 41A and 41B, the operating lever for control valve 24, squeeze air pump 21, volume bladder 22 and associated tubing 23. All other components of training device 10 are located below panel 12 but readily accessible by lifting panel 12 out of carrying Case 11.

Figure 2:
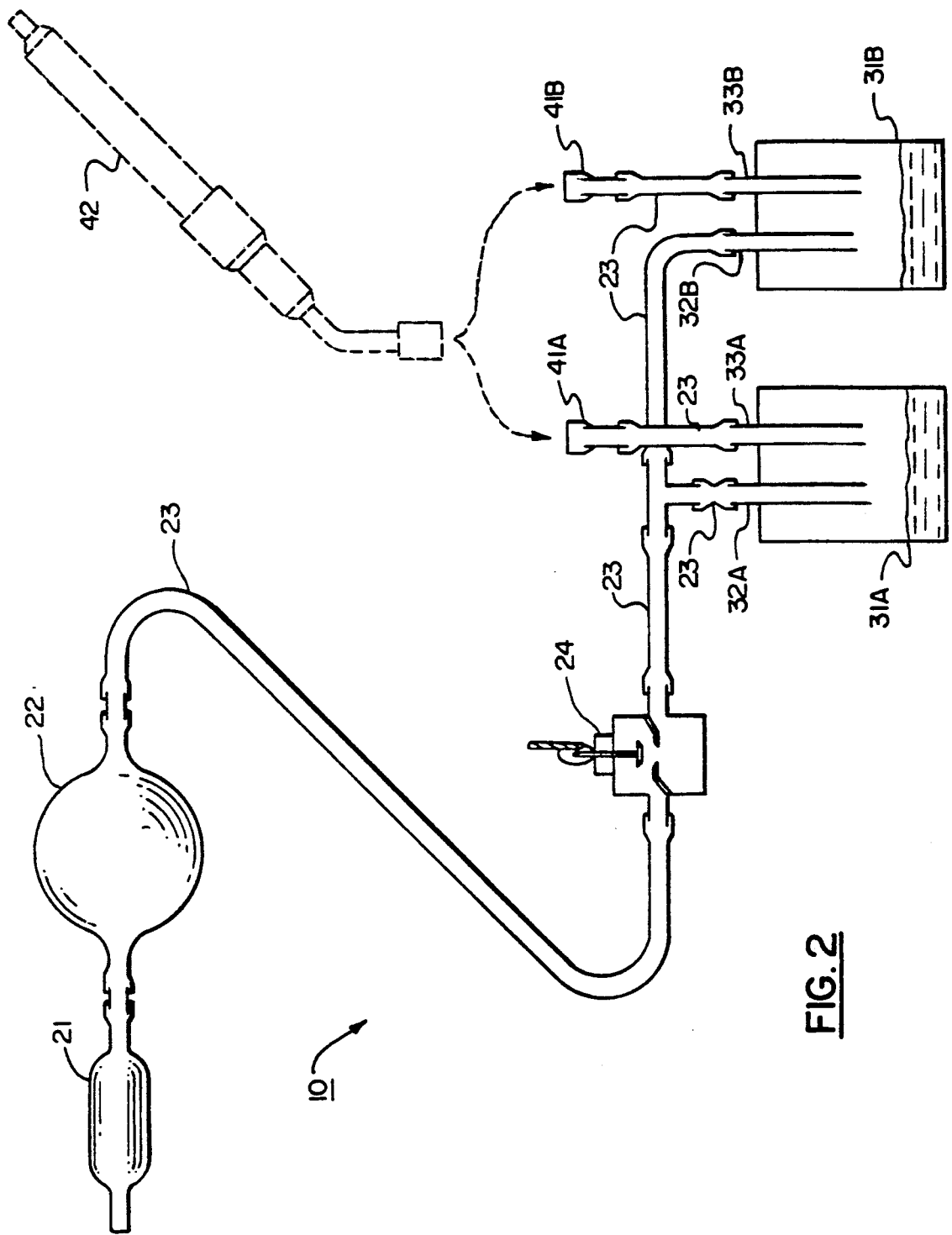
FIG. 2 is a schematic diagram of the device depicted in FIG. 1.

The operation of training device 10 is best described by reference to FIG. 2, a schematic diagram of the device depicted pictorially in FIG. 1. Located under panel 12 (FIG. 1) are contaminant sample containers 31A and 31B and manually operated control valve 24. Lengths of tubing 23 connect control valve 24 with inlets 32A and 32B of sample containers 31A and 31B respectively, outlet 33A of sample container 31A with tester connection 41A, outlet 33B of sample container 31B with tester connection 42B and volume bladder 22 with control valve 24.

Training device 10 is prepared for a demonstration or training session by placing a small amount of the contaminant of interest in either sample container 31A or 31B. A small amount of another contaminant can be placed in the other sample container if desired. For demonstrating the TOTALTEST ® tester, one sample container holds water and the other a suitable inorganic acid. With control valve 24 closed, squeeze air pump 21 is operated to fill volume bladder 22 and thus produce a store of air at a slight pressure above ambient. The gas contaminant testing apparatus, such as TOTALTEST ® testing tube holder 42, into which has been placed a contaminant testing tube containing appropriate reagent chemicals (not shown), is connected to either of tester connections 41A or 41B depending upon the contaminant indication to be demonstrated. The tester connection 41A or 41B not in use remains capped off.

To demonstrate the procedure for detecting the contaminant in sample container 31A for example, the tester is connected to tester connection 41A and tester connection 41B is capped. To commence the demonstration, control valve 24 is opened, thus admitting a flow of air from volume bladder 22 into sample container 31A through container inlet 32A. In the container, air mixes with vapor of the volatile liquid contaminant contained in the container. The mixture of air and vapor then flows out of sample container 31A through container outlet 33A and tester connection 41A into testing tube holder 42 and through the testing tube, where the mixture contacts the indicating reagent chemicals. The reagent chemical sensitive to the contaminant in sample container 31A will produce an appropriate indication. To halt the demonstration, control valve 24 is shut. To demonstrate a test for the contaminant contained in sample container 31B, the testing apparatus is connected to tester connection 41B, tester connection 41A is capped off and the procedure used for container 31A is repeated using container 31B. The store of air in volume bladder 22 may be replenished as required using squeeze air pump 21.

One skilled in the art will readily appreciate that a multitude of variations to the embodiment of the present invention described above are possible. For example, a single testing device may be fitted with more than two sample containers and there may be a separate control valve for each sample container. Sample containers may be made for containing not only volatile liquids but also contaminant gases and even solid contaminant sources and may be field refillable or non-refillable. A powered air pump may be used in place of the manually operated squeeze pump and volume bladder or the device may use a small pressure cylinder of an appropriate gas such as air, nitrogen or an inert gas to serve as the demonstration gas supply. Appropriate adapter fittings may be supplied to allow connection to the device of testing apparatus of various types.

Diagnostic training is also possible by placing more than one contaminant in a single sample container so that a trainee may gain experience in identifying contaminants present in a gas medium by analysis of tester tube readings and indications. Training in quantitative as well as qualitative analysis is possible by the provision of flow regulating orifices or other devices such as diffusion or permeation tubes containing selected contaminants.

The device of the present invention is also adaptable to use in conducting gas analyses. Rather than using testing apparatus in an atmosphere containing the gas to be tested, a small sample of the gas can be collected in a container at the source and removed to a convenient location such as a laboratory or office for analysis using the tester training device as gas handling and control auxiliary to a testing apparatus.

It is intended therefore that the scope of the invention be limited only by the scope of the below claims.

What is claimed is:

1. A device for gas contaminant testing apparatus demonstration and training comprising:
    a contaminant sample container having an inlet and an outlet;
    a testing apparatus interface;
    a demonstration gas supply;
    means for conducting a demonstration gas from said demonstration gas supply through said inlet into said sample container;
    means for causing a flow of said demonstration gas through said conducting means into said contaminant sample container;
    means for controlling the flow of said demonstration gas through said gas conducting means;
    means, within said contaminant sample container, for forming a mixture of said demonstration gas and a gaseous or vaporous contaminant; and
    means for conducting said mixture of demonstration gas and contaminant from said outlet to said interface.

2. The device of claim 1 in which said demonstration gas is air.

3. The device of claim 2 in which said gas supply comprises an air pump.

4. The device of claim 3 in which said gas supply further comprises a volume bladder.

5. The device of claim 4 in which said interface comprises a connection for attaching said testing apparatus to said training device.

6. The device of claim 1 further comprising a container in which all other components of said device are mounted or packed.

7. A training device, for demonstrating the use of a refrigerant tester comprising:
  a demonstration gas supply;
  a contaminant sample container having
    an inlet and
    an outlet;
  means for conducting a flow of gas from said demonstration gas supply to said contaminant sample container;
  means for causing a flow of said demonstration gas through said conducting means into said contaminant sample container;
  means for controlling the flow of said demonstration gas through said conducting means;
  means, within said contaminant sample container, for forming a mixture of said demonstration gas and a gaseous or vaporous contaminant;
  a refrigerant tester interface; and
  means for conducting said mixture of demonstration gas and contaminant from said outlet to said interface.

* * * * *